United States Patent [19]

Brazdil et al.

[11] 4,212,766

[45] Jul. 15, 1980

[54] PROCESS FOR FORMING MULTI-COMPONENT OXIDE COMPLEX CATALYSTS

[75] Inventors: James F. Brazdil, Lyndhurst; Dev D. Suresh, Macedonia; Robert K. Grasselli, Chagrin Falls, all of Ohio

[73] Assignee: The Standard Oil Company, Cleveland, Ohio

[21] Appl. No.: 898,356

[22] Filed: Apr. 21, 1978

Related U.S. Application Data

[63] Continuation-in-part of Ser. No. 823,319, Aug. 10, 1977, Pat. No. 4,148,757.

[51] Int. Cl.$^2$ .................... B01J 23/16; B01J 23/28; B01J 23/30; B01J 23/72

[52] U.S. Cl. .................... 252/432; 252/437; 252/439; 252/456; 252/458; 252/462; 252/465; 252/467; 252/468; 252/469; 252/470; 568/476; 260/465.3

[58] Field of Search .............. 252/432, 437, 439, 462, 252/465, 467, 468, 469, 470, 456, 458; 260/465.3

[56] References Cited

U.S. PATENT DOCUMENTS

| | | | |
|---|---|---|---|
| 3,895,051 | 7/1975 | Umemura et al. | 252/467 X |
| 3,951,861 | 4/1976 | Shiraishi et al. | 252/467 X |
| 4,040,978 | 8/1977 | Li | 252/470 X |

*Primary Examiner*—W. J. Shine
*Attorney, Agent, or Firm*—John E. Miller, Jr.; Herbert D. Knudsen; Larry W. Evans

[57] ABSTRACT

In the manufacture of a complex bismuth molybdate catalyst, bismuth molybdate is preformed prior to addition to the other ingredients in the catalyst.

11 Claims, No Drawings

PROCESS FOR FORMING MULTI-COMPONENT OXIDE COMPLEX CATALYSTS

CROSS-REFERENCE TO RELATED APPLICATION

The present invention is a continuation-in-part of application Ser. No. 823,319, filed Aug. 10, 1977, now U.S. Pat. No. 4,148,757 the disclosure of which is incorporated herein by reference.

BACKGROUND OF THE INVENTION

The present invention relates to catalysts useful in the oxidation and/or ammoxidation of olefins. More specifically, the present invention relates to a novel process for producing oxidation and/or ammoxidation catalysts having superior properties.

In the commercial preparation of molybdate catalysts, it is customary to form molybdates of the metal ions in the catalysts on the site of the catalyst preparation. In other words, metal components of the catalysts are not normally obtained from suppliers in the form of molybdates, but rather in the form of more readily available salts (hereinafter referred to as "source salts") such as nitrates. At the site of catalyst preparation, these nitrates are combined with a molybdenum and/or tungsten containing salt, such as ammonium heptamolybdate, to form aqueous solutions or slurries containing molybdates and/or tungstates of the catalyst metals as well as heat-decomposable by-product salts such as ammonium nitrate. Hereinafter, these slurries or solutions will be referred to as pre-catalyst aqueous slurries or solutions. Thereafter these molybdates and/or tungstates are assembled together to form a precatalyst precipitate which is then dried and calcined to form the objective catalyst.

U.S. Pat. No. 4,040,987 describes a novel process for producing bismuth molybdate catalysts of known composition. According to that patent, the catalytic properties of the catalysts obtained are superior when at least one element of the catalyst selected from cobalt, nickel and iron is preformed into a molybdate, and then this preformed molybdate together with a bismuth oxide or salt is formed into a precatalyst aqueous slurry, which in turn is processed conventionally to yield the objective catalyst. In Example 1, this patent shows a catalyst preparation in which cobalt nitrate, nickel nitrate and iron nitrate are each individually preformed and these preformed molybdates then admixed with preformed bismuth molybdate (the bismuth salt) and water to form the precatalyst aqueous slurry.

An essential feature of the process described in this patent is that the precatalyst aqueous slurry must be essentially free of ammonium nitrate, which is a heat-decomposable by-product formed when the various molybdates incorporated into the slurry are formed. In order to obtain this, it is necessary to filter and optionally wash the molybdates (either individually or after being combined) to remove their mother liquors and then add additional water to make up a new slurry.

Although the procedure described in U.S. Pat. No. 4,040,978 may be able to produce catalysts with improved properties, it has many features making it disadvantageous commercially. Thus, if all the molybdates are individually preformed and filtered, the process would entail too many physical steps to be practicable. In this regard, it should be appreciated that filtering of molybdate slurries can be very difficult because of the very fine physical nature of the material being filtered. On the other hand, if two or more preformed molybdates are filtered together, control of the composition of the objective catalyst becomes difficult. In this regard, it should be remembered that each different molybdate in an aqueous molybdate slurry exhibits its own equilibrium conditions, the equilibrium depending mainly upon pH. Therefore, some molybdate will inevitably remain in the mother liquor and be lost from the system when the slurry is filtered. Thus, it will be appreciated that regardless of the particular procedure adopted, producing a catalyst derived from an aqueous slurry substantially free of ammonium nitrate in accordance with the requirements of U.S. Pat. No. 4,040,978 is commercially disadvantageous.

Accordingly, it is an object of the present invention to provide a novel process for forming catalysts and in particular bismuth molybdate catalysts which can be easily practiced and still provide catalysts with improved catalytic properties.

SUMMARY OF THE INVENTION

This and other objects are accomplished by the present invention which is based on applicants discovery that catalysts of improved catalytic properties can be obtained if the bismuth molybdate component of the catalyst is separately produced and then the preformed bismuth molybdate is combined with the other elements of the catalyst to form the ultimate catalyst product.

Thus, applicants have discovered that contrary to the teachings in U.S. Pat. No. 4,040,978, what is important to improved catalytic properties is preforming the bismuth molybdate specie of the catalyst, not the cobalt, nickel and/or iron molybdate specie and that if the bismuth molybdate specie is preformed then the catalysts will exhibit enhanced catalytic properties even if the cobalt, nickel and/or iron contents of the catalyst are not preformed and even if the precatalyst aqueous slurry contains substantial amounts of ammonium nitrate of other heat-decomposable salt. Thus, in accordance with the present invention, the extensive filtering procedures necessary in that patent to remove heat-decomposable by-product produced during the catalyst preparation procedure can be totally avoided. Moreover, the cobalt, nickel and iron contents of the catalyst need not be individually preformed, if desired.

As a further feature of the invention, it has also be found that catalysts with improved properties can be obtained regardless of the preparational technique used, so long as bismuth molybdate or analog is preformed prior to combining with the other elements of the catalyst.

Thus, the present invention provides an improvement in the known process for producing a molybdate or tungstate activated oxide complex catalyst in which the elements of the catalyst are combined together in a precatalyst aqueous slurry, the slurry so obtained is dried to form a precatalyst precipitate, and the precatalyst precipitate is then calcined to form the catalyst, the improvement wherein: the key catalytic phase of the catalyst defined as a molybdate or tungstate of Bi, Te, Sb, Sn, Cu or mixtures thereof is preformed prior to combining with the other elements of the catalyst, provided that when one or more elements in the catalyst is supplied to the precatalyst aqueous slurry in the form of (a) a source salt having a heat-decomposable cation or anion, (b) an inorganic salt reaction product of the source salt, or (c) an aqueous slurry of either (a) or (b) then the elements of the catalyst are combined in such a way that the precatalyst precipitate contains a substantial amount of at least one of the heat-decomposable anions or cations.

More particularly, the present invention provides an improvement in the known process for forming a molybdate or tungstate oxide complex catalyst in which an aqueous slurry containing (1) molybdates and/or tungstates of at least some of the elements in the catalyst and (2) at least one heat-decomposable component is dried to form a precatalyst precipitate and the precipitate is then calcined to produce the catalyst, the improvement in accordance with the present invention comprising preforming the key catalytic phase of the catalyst, the key catalyst phase being defined as a molybdate and/or tungstate of Bi, Te, Sb, Sn, Cu or mixtures thereof prior to combining with the other elements of the catalyst, and further comprising drying the aqueous slurry without filtration so that the precipitate contains the heat-decomposable component.

DETAILED DESCRIPTION

The inventive catalyst preparation technique is applicable to a wide variety of different types of catalysts, the compositions of which are generally well known. Such catalysts can be described by the following general formula:

$$[M_m N_n O_x]_q [A_a C_b D_c E_d F_e N_f O_y]_p$$

wherein:
M = Bi, Te, Sb, Sn, and/or Cu
N = Mo and/or W
A = alkali, Tl, and/or Sm
C = Ni, Co, Mn, Mg, Be, Ca, Sr, Ba, Zn, Cd and/or Hg
D = Fe, Cr, Ce, and/or V
E = P, As, B, Sb
F = rare earth, Ti, Zr, Nb, Ta, Re, Ru, Rh, Ag, Au, Al, Ga, In, Si, Ge, Pb, Th, and/or U, and further wherein:
a = 0-4
b = 0-20
c = 0.01-20
d = 0-4
e = 0-8
f = 8-16
m = 0.01-10
n = 0.1-30,
a+b+c+d+e > 0, and
x and y are numbers such that the valence requirements of the other elements for oxygen in the key catalytic phase and the host-catalyst phase, respectively are satisfied; and the ratio q/p is 0.1 to 10, preferably 0.5-4.

In such catalysts, the portion denoted by $$[M_m N_n O_x]$$

is denoted as the key catalytic phase, while the portion of the catalyst defined by $$[A_a C_b D_c E_d F_e Mo_f O_y]$$

is the host-, promoter-, and/or co-catalyst phase (hereinafter referred to as the co-catalyst phase).

In this connection, although the foregoing catalyst description indicates that the catalysts produced by the inventive process are composed of two phases, namely a key catalytic phase and a host-catalyst phase, this terminology is used for descriptive purposes only. Oxide catalysts of the type described are well known in the art and normally take the form of some type of oxide complex, the specific structure of which is extremely complex and not completely understood. The catalysts produced by the inventive process are of a similar nature. More specifically, they are not composed of a simple mixture of the key and host-catalyst phases but rather a complex composition in which the key and host-catalyst phases interact with one another and which may be composed of one or more phases.

Thus it should be appreciated that the formula $$[M_m N_n O_x]_q [A_a C_b D_c E_d F_e N_f O_y]_p$$

is empirical and could just as easily have been written $$A_a C_b D_c E_d F_e M_m N_t O_r$$

(where q = p and t = n+f) since both formulas mean the same thing. This is most easily understood by referring to the two catalysts employed in the following Comparative Example A and Example 1. The two different formulas used in these examples describe the same thing, i.e. catalysts having the same chemical composition. Use of the bifurcated formulas herein is not intended to imply that the catalysts referred to have any particular type of structure, but is rather adopted for the sake of convenience and ease of description.

In the foregoing formula, M is preferably Bi and N is Mo. Preferred catalysts are those containing iron, bismuth and molybdenum and optionally phosphorus. Of these catalysts, those containing nickel, cobalt and iron and optionally phosphorus or antimony, are preferred, and of these catalysts those containing an alkali metal, most preferably potassium, rubidium and/or cesium, are especially preferred. Also, if the catalyst contains a Group IIA or IIB metal, it is preferably selected from the Group consisting of Mg, Cd, and Zn.

An important feature of the present invention as indicated above is that the key catalytic phase of the catalyst, for example bismuth molybdate, is preformed prior to combining with the other elements of the catalyst. The key catalytic phase can be made in accordance with any conventional technique. For example, bismuth molybdate can be conveniently prepared by adding ammonium heptamolybdate, $(NH_4)_6Mo_7O_{24}\cdot 4H_2O$, to an aqueous solution of bismuth nitrate, preferably in a nitric acid solution, and then adjusting the pH to form a precipitate of bismuth molybdate. An aqueous solution of $MoO_3$ in $NH_4OH$ can also be used in place of the ammonium heptamolybdate. Furthermore, other bismuth salts having decomposable anions can be employed. For example, acetate, triphenyl, citrate and so forth salts of bismuth can be employed to form bismuth molybdate. Similarly, decomposable salts of the other M elements can be used to supply the M component of the key catalytic phase, while ammonium tungstate, tungstic acid and the like can be used to supply tungsten in the case in which N is W.

Still another technique for forming the key catalytic phase is by known metallurgical techniques, for example, by reacting bismuth oxide and molybdenum oxide together in the solid phase or by refluxing an aqueous slurry of the respective oxides.

Preparation of molybdates and/or tungstates of the various elements M listed in the foregoing formula are well known in the art. Thus those skilled in the art should be able to produce the preformed catalytic phase of the catalyst of the inventive process with no difficulty.

In producing the key catalytic phase of the objective catalysts, the amount of M and N components combined together is, of course, dependent upon the ultimate composition of the objective catalyst as well as the amount of N element in the co-catalyst phase. Within this framework, however, it is desirable that the ratio M/N in forming the key catalytic phase be maintained within the range of 1:9 to 9:1, preferably 2:1 to 1:3 and most preferably 2:1 to 2:3. When producing bismuth molybdate as the key catalytic phase, it is especially preferred that the M/N ratio be 2:1 to 1:3 and most preferably 2:1 to 2:3.

Once the key catalytic phase is formed, the other elements of the objective catalyst are added thereto to form a precatalyst ready for calcination. This can be accomplished by essentially any manner.

For example, simple oxides of all the elements of the co-catalyst phase can be intimately combined with the preformed key catalytic phase by metallurgical techniques (e.g. ball milling) to form the precatalyst.

Usually, however, the precatalyst is made by slurry techniques wherein the preformed key catalytic phase together with all of the other ingredients in the catalyst are combined in the form of an aqueous slurry which is heated to evaporate the water therefrom and produce a dried precatalyst precipitate.

As an example of this procedure, the easiest way to combine the other components of the catalyst with the key catalytic phase is described in the parent application and comprises forming molybdates and/or tungstates of most or all of the ingredients of the cocatalyst phase in a single slurry containing all of the cocatalyst ingredients, adding the cocatalyst slurry to the key catalytic phase, and then drying and calcining the slurry produced. Commercially, this is the most advantageous procedure because it involves the least amount of process steps.

Another easy way to form the precatalyst using slurry techniques is to add some or all of the elements of the catalyst other than those in the key catalytic phase to the preformed key catalytic phase in the form of salts having heat-decomposable anions or cations, these salts being added either as solids, solutions or slurries. In other words, rather than mixing up a cocatalyst phase solution or slurry separately, this can be done in the same vessel containing the key catalytic phase solution or slurry. This method is exemplified in the following Example 3.

In still another method, one or more of the elements in the cocatalyst phase can be individually formed into molybdates and/or tungstates and then added either in the form of solids, solutions or slurries to the host catalyst. This method is illustrated in the following Example 6.

Once the aqueous slurry containing all of the ingredients of the objective catalyst is formed, the slurry is heated to drying to form the precatalyst. In accordance with well known chemical phenomena, heating, pH adjustment or other appropriate treatment of the aqueous composition causes precipitation of the components dissolved in the liquid phase of the slurry, thereby producing a precipitate which together with the preformed key catalytic phase forms a precatalyst of appropriate composition.

The precatalysts of the present invention are calcined prior to use. As is well known in the art, calcination of oxide complex precatalysts serves to activate the catalysts, i.e. change the precatalyst oxide mixture with essentially no catalytic activity to the finished oxide complex catalyst with significant catalytic activity. Also, calcination serves to drive off decomposable anions and cations which may be present in the precatalyst. In accordance with the present invention, calcination can be accomplished in the presence of oxygen, preferably air, or other gas in a conventional manner. For example, the catalyst can be calcined for a period of $\frac{1}{4}$ to 48 hours at temperatures of 200° C. to 800° C. in the presence of air.

The starting materials used to supply particular elements for forming the precatalyst of the invention can be any materials conventionally employed in the manufacture of oxidation catalysts. Normally, decomposable salts which will yield the desired elements upon heating to elevated temperatures are employed, although oxides and even free acids can be employed as can salts in which with the anion and cation contribute elements to the ultimate catalyst such as $KH_2PO_4$. For example, nitrate, acetate, triphenyl and citrate salts of the elements in question can be employed as can phosphoric acid, antimony oxide and chromium trioxide. Nitrate salts find particular applicability in prior art processes and are especially useful in the inventive process.

Techniques for forming oxide complex catalysts containing a wide variety of different elements and based on molybdates or tungstates are well known in the art, and those skilled in the art should have no difficulty in determining how to incorporate a particular element into the catalyst of the present invention. So long as the key catalytic phase of the objective catalyst is preformed, the objective catalyst produced will have excellent catalytic activity.

The catalyst of the present invention may include significant amounts of essentially inert supports such as silica, alumina, alundum, pumice, titania, zirconia and the like. Such support materials are well known in the art for supporting oxide complex type catalysts, and any conventional support material can be employed in any conventional amount. When a support material is employed, it can be added to the remaining ingredients of the objective catalyst at any time and in any manner. For example, the support material can be added to the key catalytic phase prior to the addition of the co-catalyst phase or it can be added to the catalyst once formed before or even after calcination. Preferably, however, the support material is added to the co-catalyst prior to combining the co-catalyst phase with the key catalytic phase if the co-catalyst phase is separately prepared. If the co-catalyst phase is prepared in the same vessel as contains the key catalytic phase, the support can be added together with any of the ingredients used to form the co-catalyst phase or separately.

An important feature of the present invention as indicated above is that the key catalytic phase of the objective catalyst is preformed prior to admixing with the other ingredients of the catalyst. Although not wishing to be bound in any theory, applicants believe that prior art processes for making molybdate and/or tungstate catalysts were disadvantageous because the element or elements M (e.g. Bi) had to compete with the other elements in the catalyst (e.g. Ni, Co or Fe) for molybdenum and/or tungsten as the molybdate and/or tungstate species were formed. In accordance with the present invention, however, the M element is allowed to form a molybdate and/or tungstate without competition from competing elements so that the key catalytic phase can properly form. As a result, the catalysts produced by the inventive process have superior catalytic activity compared to catalysts produced by prior art techniques in which molybdate or bismuth are formed together with molybdates of other metals in the catalysts.

In the preferred embodiment of the invention as described above many and in some instances all of the elements of the catalyst are supplied to inventive catalyst preparation technique in the form of salts having heat-decomposable anions or cations, for example nitrates and ammonium salts. When these various salts are combined together, usually in the form of an aqueous slurry, heat-decomposable salts form as by-products. For example, when bismuth molybdate is made by reacting ammonium heptamolybdate with bismuth nitrate, ammonium nitrate forms as a by-product salt. In accordance with the invention, it is desirable not to remove these heat-decomposable by-product salts from the catalyst ingredients prior to the calcination procedure.

In this regard, U.S. Pat. No. 4,040,978 as indicated above does show examples in which the catalyst preparation includes performing bismuth molybdate as accomplished in the present invention. However, in the catalyst preparations shown in that patent, many and in some instances all of the metals in the catalyst are supplied from source compounds containing heat-decomposable cations or anions, and it is specifically taught that these ions must not be present in the precatalyst precipitate which is calcined to produce the ultimate catalyst. Thus, a critical feature of the invention in U.S. Pat. No. 4,040,978 is filtering to remove these ions (or salts thereof) before the precatalyst precipitate is calcined. Since, however, this patent does disclose preforming bismuth molybdate, the present invention in order to distinguish over U.S. Pat. No. 4,040,978 is characterized by the further proviso that if any of the metals in the catalyst are supplied to the catalyst preparation from one or more source compounds containing heat-decomposable anions or cations, then the metals of the catalyst are combined in such a way that the precatalyst precipitate subjected to calcination contains a substantial amount of at least one of the heat-decomposable cations or anions. And by "substantial amount" is meant more than the impurity amounts of ammonium nitrate which might be present in the precatalyst precipitates of U.S. Pat. No. 4,040,978.

In other words, in the embodiment of the inventive process in which at least one of the starting materials for catalyst preparation is a salt containing a heat-decomposable cation or anion, the extensive filtering procedures described in U.S. Pat. No. 4,040,978 for removing heat-decomposable ammonium nitrate from the catalyst ingredients and producing a precatalyst essentially free of ammonium nitrate are avoided. In accordance with the present invention, it has been found that catalysts having essentially the same good catalytic effectiveness as those produced by the process of U.S. Pat. No. 4,040,978 can be obtained by the inventive process even though the precatalyst subjected to calcination contains significant amounts of one or more heat-decomposable by-product salts. Thus, the procedure of the inventive process in the embodiment in which at least one of the starting materials for catalyst preparation is a salt containing a heat-decomposable cation or anion is exactly the opposite of the procedure described in U.S. Pat. No. 4,040,978.

In order that the precatalyst subjected to calcination contains a substantial amount of heat-decomposable anion or cation in accordance with the preferred embodiment of the invention, all that is necessary is that at least one of the source compounds containing a heat-decomposable anion or cation be processed in such a way that the heat-decomposable anion or cation is not removed from its associated catalyst ingredient during the precatalyst preparation and drying. In conventional catalyst preparation, the source salts are usually formed into the precatalyst precipitate by either (1) adding the source salt itself to the other ingredients, (2) causing the source salt to react to form another inorganic salt reaction product (e.g. $Fe(NO_3)_2 + (NH_4)_2Mo_7O_{24} \cdot 6H_2O \rightarrow Fe_2(MoO_4)_3 + NH_4NO_3$) and then adding this inorganic salt reaction product (in this case $FeMoO_3$) to the other ingredients, or (3) adding the salt of (1) or the reaction product salt of (2) in the form of aqueous slurries to the other ingredients. These same techniques can be used in the inventive catalyst preparation process so long as not all of the heat-decomposable anions and/or cations are removed from the system prior to formation and drying of the precatalyst precipitate.

SPECIFIC EMBODIMENTS

In order to more thoroughly illustrate the present invention and its relation to the prior art, the following experiments are presented:

Comparative Example A

A catalyst of the formula:

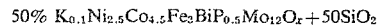

50% $K_{0.1}Ni_{2.5}Co_{4.5}Fe_3BiP_{0.5}Mo_{12}O_x$ + 50$SiO_2$ was prepared by a conventional catalyst preparation technique in the following manner:

36.36 g $FeNO_3 \cdot 9H_2O$ was added to approximately 10 cc $H_2O$ and warmed by a hot plate until it dissolved/melted. Next, 14.55 g $BiNO_3 \cdot 5H_2O$ was added to the solution and allowed to dissolve/melt therein. Thereafter 39.29 g $Co(NO_3)_2 \cdot 6H_2O$ was added to the solution and allowed to dissolve/melt. Next, 21.81 g $Ni(NO_3)_2 \cdot 6H_2O$ was added and allowed to dissolve/melt. Then 3.03 g of 10 weight percent $KNO_3$ aqueous solution was added to form a dark brown solution denoted as solution A.

In a separate container, 63.56 g $(NH_3)_6Mo_7O_{24} \cdot 4H_2O$ was dissolved in 65 cc $H_2O$ at 60° C. 205.49 g of a 40 percent silica sol (Nalco) was added to the dissolved ammonium heptamolybdate. Next 3.46 g of a 42 percent $H_3PO_4$ aqueous solution was added to form a slurry denoted as composition B.

Nitrate solution A was then slowly added with stirring to composition B and as a result a light yellow slurry was formed. The slurry was heated and stirred until it thickened. The thickened material was dried to 120° C. and then denitrified by heating in air at 290° C. for three hours followed by heating in air at 425° C. for three hours. The catalyst was then ground to 20 to 35 mesh size and the ground catalyst was calcined in air at 610° C. for three hours to yield the objective catalyst.

EXAMPLE 1

A catalyst having the following chemical formula was prepared by the process of the present invention:

50% [Bi$_2$Mo$_3$O$_{12}$]$_{\frac{1}{2}}$[K$_{0.1}$Ni$_{2.5}$Co$_{4.5}$Fe$_3$P$_{0.5}$Mo$_{10.5}$O$_x$] + 50% SiO$_2$ As will be noted, the chemical composition of this catalyst is identical to the chemical composition of the catalyst made in Comparative Example A.

14.55 g Bi(NO$_3$)$_3$.5H$_2$O was dissolved in 100 ml. of a 10 percent HNO$_3$ aqueous solution. 7.95 g of (NH$_4$)Mo$_7$O$_{24}$.4H$_2$O was dissolved in 100 ml. H$_2$O with heating. The bismuth nitrate solution was then slowly added to the ammonium heptamolybdate solution with constant stirring. The pH was then adjusted to 2.5 to 3 by the addition of NH$_4$OH. The mixture was stirred for about one hour, thereby yielding a bismuth molybdate slurry.

In a separate container, 3.03 g of a 10 percent KNO$_3$ aqueous solution, 21.81 g Ni(NO$_3$)$_2$.6H$_2$), 39.29 g Co(NO$_3$)$_2$.6H$_2$O and 36.36 g Fe(NO$_3$)$_3$.9H$_2$O were added to 50 ml. of water with heating. Next 55.61 g (NH$_4$)$_6$Mo$_6$O$_{24}$.4H$_2$O was dissolved in 150 ml. of water with heating and to this solution was added 3.46 g of a 42.5 percent aqueous solution of H$_3$PO$_4$ and 205.49 g of a 40 percent silica sol (Nalco). Next, the metal nitrate solution was added to the ammonium heptamolybdate/phosphoric acid solution and the mixture obtained stirred for one to two hours at 90° C. to form a host-catalyst slurry.

The previously prepared bismuth molybdate slurry was then added to the host-catalyst slurry with stirring. The mixture obtained was evaporated to dryness with constant stirring on a hot plate and finally in a drying oven at 120° C. The dried material was then calcined in air at 290° C. for three hours, then 425° C. for three hours, then ground and screened to 20 to 35 mesh particle size. The ground material was then finally calcined at 610° C. for a period of three hours to yield the objective catalyst.

EXAMPLE 2

Example 1 was repeated except that the bismuth molybdate slurry was filtered to remove the preformed bismuth molybdate from the mother liquor. The bismuth molybdate was then dried overnight, calcined in the air at 290° C. for one hour and ball milled before being added to the hostcatalyst slurry.

In order to compare the catalytic properties of the catalysts produced above, a series of experiments was conducted in which propylene was ammoxidized to acrylonitrile. In these experiments, 5 cc of each of the above catalysts was individually charged into a plug flow microreactor and a feed comprising 1.80 propylene/2.20 NH$_3$/2.94 air/2.88 O$_2$5.89 H$_2$O was fed to the reactor. The reaction temperature was maintained at 430° C. and the feed was fed to the reactor such that the contact time of the reaction was 6 seconds. The results obtained are set forth in the following Table I. In this and following tables, yield is defined as:

$$\% \text{ yield} = \frac{\text{moles product produced}}{\text{moles propylene fed}}$$

TABLE I

| Catalyst | NH$_3$ burned | Acrylonitrile yield | HCN yield |
|---|---|---|---|
| Comp (A) | 16.4 | 72.7 | 2.8 |
| Ex. 1 | 9.0 | 78.0 | 4.6 |
| Ex. 2 | 11.9 | 75.8 | 2.8 |

From the foregoing table, it can be seen that the yield of the desired product, acrylonitrile, as well as useful by-product HCN undergo a significant increase when the catalyst is produced in accordance with the inventive process. It will also be noted that the amount of NH$_3$ burnt is significantly reduced, which means significantly less NH$_3$ is wasted through the formation of NO$_2$ and N$_2$. And since the amount of ammonia burnt when using molybdate and tungstate catalysts in ammoxidation reactions tends to decrease with time, even greater ammonia savings can be expected than exemplified above. These advantages as well as the fact that inventive process is simple and easy to carry out make the present invention of significant commercial importance.

In order to further compare the catalytic properties of the catalysts produced by the present invention with prior art catalysts, two additional experiments involving the oxidation of propylene to acrolein and acrylic acid were conducted. In these experiments, 5 cc each of the catalysts of Example 1 and Comparative Example A were separately changed into a 5 cc flug flow, fixed-bed reactor. A feed comprising 1 propylene/11 air/4H$_2$O was fed to the reactor in each test at a temperature of 350° C. and a contact time of 3 seconds. The results obtained are set forth in the following Table II.

TABLE II

| Catalyst | Acrolein Yield | Acrylic Acid Yield | Sum of Acrolein & Acrylic Acid Yields |
|---|---|---|---|
| Comp (A) | 78.3 | 3.8 | 82.1 |
| Example 1 | 78.3 | 8.1 | 86.4 |

As can be seen, the yield of acrylic acid significantly increase when a catalyst of the present invention is used.

As mentioned above, U.S. Pat. No. 4,040,978 discloses a catalyst preparation technique in which an aqueous slurry of individually preformed molybdates which is substantially free of nitrates is calcined to form the objective catalyst. One of the advantages indicated in that patent is realized from the specific preparation technique disclosed is that acrylonitrile can be produced with better selectivity and yield. The following Comparative Example B and Example 3 are presented to show that the catalytic properties of catalysts produced by the inventive process are as good as or even better than those of the catalysts obtained in the prior patent.

COMPARATIVE EXAMPLE B

Mo$_{10}$Co$_{3.41}$Ni$_{1.9}$Bi$_{0.75}$Fe$_{2.26}$P$_{0.40}$K$_{0.32}$O$_x$ + 50% SiO$_2$

A catalyst with the foregoing composition was prepared according to the manner disclosed in Example I of U.S. Pat. No. 4,040,978 as follows:

First, the following molybdates were prepared by double decomposition and precipitation from ammonium molybdate solutions.

NiMoO$_4$ 10.365 g of MoO$_3$ were dissolved in a solution of 100 ml. of H$_2$O and 11.88 ml. of concentrated reagent grade NH$_4$OH. A solution of 20.94 g of Ni(NO$_3$)2.6H$_2$O in 50 ml. H$_2$O was slowly added with constant stirring. The mixture was boiled for 2 hours.

CoMoO$_4$ 19.50 g of MoO$_3$ were dissolved in a solution of 179.2 ml. of H$_2$O and 21.29 ml. of concentrated reagent grade NH$_4$OH. A solution of 39.42 g of Co(NO$_3$)2.6H$_2$O in 112.50 ml. of H$_2$O was slowly added with constant stirring. The mixture was boiled for 2 hours.

Fe$_2$(MoO$_4$)$_2$ 18.46 g of MoO$_3$ were dissolved in a solution of 169.7 ml. of H$_2$O and 20.17 ml. of concentrated reagent grade NH$_4$OH. A solution of 34.54 g of Fe(NO$_3$)$_3$.9H$_2$O in 125 ml. of H$_2$O was slowly added at room temperature with constant stirring.

Bi$_2$(MoO$_4$)$_3$ 6.15 g of MoO$_3$ were dissolved in a solution of 59.43 ml. of H$_2$O and 6.73 ml. of concentrated reagent NH$_4$OH. A solution of 13.82 g of Bi(NO$_3$)$_3$.5H$_2$ in 74.25 ml. of H$_2$O and 5.2 ml. of concentrated reagent grade HNO$_3$ was added with constant stirring. The pH of the mixture was adjusted to 6.0 by the dropwise addition of NH$_4$OH.

Next, the ferric molybdate and bismuth molybdate slurries were combined together and filtered with suction. Thereafter the cobalt molybdate and nickel molybdate slurries were mixed and poured through the same filter on top of the ferric and bismuth molybdates. The precipitates were then washed with 250 ml. of H$_2$O and then slurried in a sufficient amount of H$_2$O. To this slurry was added 187.50 g of Nalco 40% SiO$_2$ sol with constant stirring.

A solution of 3.94 g of K$_2$MoO$_4$.5H$_2$O dissolved in 16.3 ml. of H$_2$O was added to the slurry followed by the dropwise addition of 3.46 g of 42.5% of H$_3$PO$_4$. The mixture was evaporated to dryness on a hot plate with constant stirring at 120° for 16 hours.

The dried material was calcined in the presence of oxygen at 290° C. for 3 hours and then at 425° C. for 3 hours. It was then ground again and screened to 20–35 mesh particle size and finally calcined at 550° C. for 3 hours.

EXAMPLE 3

A catalyst having an identical composition to the catalyst of Comparative Example B was made by the procedure of the present invention in the following manner:

10.91 g Bi(NO$_3$)$_3$.5H$_2$O was dissolved in about 40 ml. of a 10% aqueous HNO$_3$ solution. 5.96 g of (NH$_4$)$_6$Mo$_7$O$_{24}$.4H$_2$O was dissolved in about 75 ml. of H$_2$O with heating. The bismuth nitrate solution was added with constant stirring to the ammonium heptamolybdate solution. The pH of the mixture was then adjusted to 2.5 to 3 by the dropwise addition of reagent grade NH$_4$OH. The mixture was then stirred for 1 hour to produce a bismuth molybdate slurry.

49.77 g of Co(NO$_3$)$_2$.6H$_2$O, 16.58 g Ni(NO$_3$)$_2$.6H$_2$O, 27.39 g Fe(NO$_3$)$_3$.9H$_2$O and 9.71 g of a 10% aqueous solution of KNO$_3$ were dissolved together in about 50 ml. of water with heating. The aqueous solution so obtained was then added to the previously formed bismuth molybdate slurry.

The remaining 47.01 g of ammonium heptamolybdate was dissolved in about 100 ml. of water with heating, and to this solution was added 2.77 g of 42.50% aqueous solution of H$_3$PO$_4$. Next, 166.31 g of a 40% Nalco silica sol was added. The resultant mixture was then added to the previously formed bismuth molybdate/metal nitrate mixture. The final mixture was then stirred at about 80° C. for 1 hour and then evaporated to dryness on a hot plate with constant stirring. Final drying was accomplished in a drying oven at 120° C. for 16 hours. The dried material was calcined at 290° C. for 3 hours and then 425° C. for 3 hours. The partially calcined material was then ground and screened to the 20–35 mesh particle size and then finally calcined at 550° C. for 2 hours.

In order to compare the catalytic properties of the two catalysts produced above, a series of experiments were conducted in which propylene was ammoxidized to acrylonitrile. In these experiments cc of each of the above catalysts was individually charged into a plug flow microreactor and a feed comprising 1.80 propylene/2.20 NH$_3$/3.60 O$_2$/2.4 N$_2$/6.0 H$_2$O was fed to the reactor with a contact time of 6 seconds. The reaction temperature of the reactions as well as the results obtained are set forth in the following Table III. In this Table, yield is defined above while selectivity is defined as:

$$\% \text{ selectivity} = \frac{\text{moles acrylonitrile produced}}{\text{moles propylene reacted}}$$

TABLE III

PROPYLENE AMMOXIDATION

| Catalyst | Reactive Temperature | % NH$_3$ Burn | % NH$_3$ Breakthrough | % O$_2$ in Effluent | % Yield Propylene | Acrylonitrile | Acrolein | Acrylic Acid | CH$_3$CN | HCN | CO | CO$_2$ | Acrylonitrile Selectivity |
|---|---|---|---|---|---|---|---|---|---|---|---|---|---|
| Example 3 | 430° C. | 18.7 | 7.3 | 10.6 | 1.5 | 76.6 | 0.5 | 1.9 | 3.2 | 4.3 | 4.2 | 7.7 | 77.8 |
| Example 3 | 445° C. | 23.1 | 7.5 | 4.9 | 0.2 | 77.0 | 0.5 | 1.2 | 2.1 | 4.5 | 4.9 | 9.6 | 77.2 |
| Comparative Example B | 430° C. | 7.2 | 11.9 | 6.3 | 0.0 | 76.9 | 0.5 | 0.8 | 1.9 | 6.0 | 3.5 | 10.5 | 76.9 |
| Comparative Example B | 445° C. | 16.5 | 14.1 | 2.0 | 0.0 | 73.3 | 0.5 | 0.8 | 1.2 | 6.3 | 6.7 | 11.3 | 73.3 |

From the foregoing Table, it can be seen that the yield of acrylonitrile realized when the catalysts of the present invention are used are at least as good as the yields obtained when catalysts made by prior art procedures are employed. Moreover, at higher temperature, the inventive catalysts are even better. In addition, it should be further noted that the selectivity to acrylonitrile of the catalysts produced by the present invention are better than those produced by the prior art catalysts. Thus, it would be readily appreciated that the inventive process even though significantly easier to carry out than the process described in U.S. Pat. No. 4,040,978, produces catalysts which are at least good as if not better than the catalysts produced by the process of that patent.

Still additional comparisons of the present invention with the prior art are shown in the following examples:

was maintained at 430° C. The results are set forth in the following Table IV.

TABLE IV

PROPYLENE AMMOXIDATION

| Catalyst | W/W/H | Contact Time (sec.) | % Break-through | % NH$_3$ Burned | % O$_2$ in Effluent | % Yield Propylene | Acrylonitrile | Acrolein | Acrylic Acid | CH$_3$CN | HCN | CO | CO$_2$ | Acrylonitrile Selectivity |
|---|---|---|---|---|---|---|---|---|---|---|---|---|---|---|
| Example 4 | 0.06 | 6 | 16.3 | 12.7 | 1.5 | 0 | 79.1 | 0.8 | 0.4 | 3.1 | 2.7 | 4.8 | 9.1 | 79.1 |
| Comparative Example C | 0.06 | 6 | 9.3 | 18.6 | 6.2 | 1.3 | 79.9 | 1.1 | 2.2 | 2.9 | 2.2 | 3.0 | 7.3 | 80.9 |
| Example 4 | 0.18 | 2 | 15.0 | 17.7 | 12.2 | 11.9 | 76.4 | 0.8 | 1.6 | 2.7 | 2.6 | 1.3 | 2.8 | 86.8 |
| Comparative Example C | 0.18 | 2 | 17.4 | 18.4 | 15.2 | 18.8 | 70.0 | 0.8 | 0.5 | 2.8 | 2.4 | 1.3 | 3.5 | 86.2 |
| Example 5 | 0.06 | 6 | 20.6 | 3.5 | 7.4 | 1.6 | 81.8 | 0.5 | 0.8 | 1.8 | 3.7 | 2.7 | 6.9 | 83.2 |
| Comparative Example D | 0.06 | 6 | 13.0 | 14.0 | 12.0 | 3.9 | 79.9 | TR | 0.9 | 1.8 | 2.9 | 2.6 | 7.9 | 83.2 |
| Example 5 | 0.18 | 2 | 13.3 | 27.5 | 24.5 | 21.8 | 67.4 | 1.0 | 0.1 | 1.6 | 2.9 | 1.4 | 3.8 | 86.2 |
| Comparative Example D | 0.18 | 2 | 28.9 | 17.4 | 22.4 | 30.2 | 60.2 | 0.7 | 0.6 | 1.6 | 2.7 | 0.9 | 3.0 | 86.4 |

EXAMPLE 4

50% Cs$_{0.05}$K$_{0.1}$Ni$_{2.5}$Co$_{4.5}$MnFe$_2$BiCr$_{0.5}$Mo$_{13.2}$O$_x$ + 50% SiO$_2$

A catalyst having the composition noted above was formed by the same procedure used to form the catalyst of Example 3 except that manganese nitrate in the form of a 50% aqueous solution was combined with the other metal nitrates prior to the addition of the metal nitrate solution to the bismuth molybdate slurry and in addition chromium oxide (CrO$_3$) was used instead of H$_3$PO$_4$. Also, final calcination was at 550° C. for 2 hours.

COMPARATIVE EXAMPLE C

A catalyst having an identical composition to the catalyst of Example 4 was prepared by the same technique employed for the preparation of the catalyst in Comparative Example A.

EXAMPLE 5

50% Cs$_{0.2}$Ni$_{2.5}$Co$_{4.5}$Fe$_3$BiSb$_{0.5}$Mo$_{12}$O$_x$ + 50% SiO$_2$

A catalyst having the foregoing composition was prepared by the same tehcnique used in the preparation of the catalyst of Example 3 except that cesium nitrate was used instead of potassium nitrate and antimony oxide (Sb$_2$O$_3$) was used in place of the H$_3$PO$_4$. Also, final calcination was conducted at 610° C. for 3 hours.

COMPARATIVE EXAMPLE D

A catalyst having an identical composition to the catalysts of Example 5 was prepared by the same technique employed in the preparation of catalyst of Comparative Example A except that the final calcination was at 590° C. for 3 hours rather than 550° C. for 2 hours.

In order to compare the catalytic properties of the various catalysts produced above, a series of experiments was conducted in which propylene was ammoxidized to acrylonitrile. In these experiments, a feed comprising propylene/NH$_3$/O$_2$/N$_2$/H$_2$O in a ratio of 1.8/2.2/3.6/2.4/6.0 was fed to a microreactor for the production of acrylonitrile. The reaction temperature From the foregoing Table, it can be seen that the yield of acrylonitrile realized when the inventive catalysts are employed are superior to the yields realized when catalysts made by conventional techniques are employed. In addition, it will be further noted that this effect is especially pronounced when the ammoxidation process is conducted with high propylene throughput. In this connection, the parameter WWH as set forth in the Table is a measure of propylene throughput and is defined as:

$$\frac{\text{weight of propylene fed}}{\text{weight of catalysts} \times \text{hour}}$$

As will be noted from the table, at higher values of WWH the catalyst produced by the inventive process gives a much superior yield of acrylonitrile.

Still another example of the inventive process is as follows:

EXAMPLE 6

50% Cs$_{0.05}$K$_{0.1}$Ni$_{2.5}$Co$_{4.5}$Fe$_2$Mn$_1$Cr$_{0.5}$BiMo$_{13.7}$O$_x$ + 50% SiO$_2$

A solution containing 12.95 grams MoO$_3$ dissolved in 11.2 grams of a 28% aqueous solution of NH$_4$OH and 22.8 grams H$_2$O was admixed with a solution of 24.24 grams Fe(NO$_3$)$_3$. 9H$_2$O in 52.5 grams H$_2$O to form an iron molybdate slurry. The slurry was mixed for three hours at 100° C.

To 12.8 grams H$_2$O were added 39.29 grams Co(NO$_3$)$_2$. 6H$_2$O, 21.81 grams Ni(NO$_3$)$_2$.6H$_2$O and 10.24 grams of a 50% aqueous solution of Mn(NO$_3$)$_2$. The solution so obtained was then added to the previously produced iron molybdate slurry.

Next, an aqueous solution of 34.55 grams MoO$_3$ dissolved in 30.1 grams of a 28% NH$_4$OH aqueous solution and 70.5 grams H$_2$O was added to the resultant slurry for the formation of cobalt molybdate, nickel molybdate and manganese molybdate.

In a separate beaker, 6.00 grams Cr(NO$_3$)$_3$.9H$_2$O was added to an aqueous solution containing 5.18 grams MoO$_3$, 4.15 grams of a 28% aqueous solution of NH$_4$OH and 10.6 grams of water to form an chromium molybdate slurry.

Next, the chromium molybdate slurry is added to the previously formed iron, cobalt, nickel, magnesium molybdate slurry to form a co-catalyst phase molybdate slurry.

In a separate beaker, a preformed bismuth molybdate slurry is prepared by dissolving 14.55 grams Bi(NO$_3$)$_3$.5H$_2$O in 5.4 grams HNO$_3$ and 3.9 grams H$_2$O, the bismuth nitrate solution then being diluted with 13.1 grams of water. To this solution is added an aqueous solution of 6.48 grams MoO$_3$ dissolved in 5.6 grams NH$_3$OH and 13.2 grams water whereby the bismuth molybdate forms.

The above preformed bismuth molybdate slurry is diluted to a concentration of about 50% by slowly adding a portion of the previously formed co-catalyst molybdate slurry thereto. The remainder of the co-catalyst molybdate slurry is then quickly added and the composition so obtained mixed for approximately 2 hours at 75°-80° C.

To the mixture so obtained is then added 224.50 grams of Nalco 40% silica sol followed by a solution of 0.29 grams CsNO$_3$ and 0.30 grams KNO$_3$ and 6.1 grams H$_2$O. The pH of the composition so obtained is then adjusted to approximately 3-4 by the addition of HNO$_3$. The slurry is then dried without filtering, heated and calcined for 3 hours at a temperature of 290° C., 3 hours at 425° C. and 3 hours at 610° C. to produce the catalyst of the invention.

5 cc of the catalyst are charged into a fixed bed microreactor and contacted with a feed comprising 1.8 propylene/2.2 NH$_3$/3.6 O$_2$/2.4 N$_2$/6.0 H$_2$O at a temperature of 430° C. and a contact time of 6 seconds with a W/W/H of 0.06. The selectivity to acrylonitrile was 84.8% while the yield of acrylonitrile was 77.1%.

Although only a few embodiments of the present invention have been described above, it should be appreciated that many modifications can be made without departing from the spirit and scope of the invention. All such modifications are intended to be included within the scope of the present invention which is to be limited only by the following claims.

We claim:

1. In a process for producing a molybdate or tungstate activated oxide complex catalyst in which the elements of the catalyst are combined together in a precatalyst aqueous slurry, the slurry so obtained is dried to form a precatalyst precipitate, and the precatalyst precipitate is then calcined to form said catalyst, the improvement wherein: the key catalytic phase of said catalyst defined as a molybdate or tungstate of Bi, Te, Sb, Sn, Cu or mixtures thereof is preformed prior to combining with the other elements of said catalyst, provided that when one or more elements in said catalyst is supplied to said precatalyst aqueous slurry in the form of
  (a) a source salt having a heat-decomposable cation or anion,
  (b) an inorganic salt reaction product of said source salt, or
  (c) an aqueous slurry of either (a) or (b)
then the elements of said catalyst are combined in such a way that said precatalyst preciptate contains a substantial amount of at least one of said heat-decomposable anions or cations, said catalyst having a composition defined by the formula:

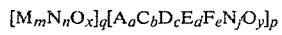

wherein
M=Bi, Te, Sb, Sn and/or Cu
N=Mo and/or W
A=alkali, Tl, and/or Sm
C=Ni, Co, Mn, Mg, Be, Ca, Sr, Ba, Zn, Cd and/or Hg
D=Fe, Cr, Ce and/or V
E=P, As, B, Sb
F=rare earth, Ti, Zr, Nb, Ta, Re, Ru, Rh, Ag, Au, Al, Ga, In, Si, Ge, Pb, Th, and/or U, and further wherein
a=0-4
b=0-20
c=0.01-20
d=0-4
e=0-8
f=8-16
m=0.01-10
n=0.1-30
a+b+c+d+e>0, and
x and y are numbers such that the valence requirements of the other elements for oxygen in the key catalytic phase and the host-catalytic phase, respectively, are satisfied; and the ratio of q/p is 0.1 to 10.

2. The process of claim 1 wherein said key catalytic phase is a bismuth molybdate.

3. In a process for forming a molybdate or tungstate oxide complex catalyst in which an aqueous slurry containing (1) molybdates and/or tungstates of at least some of the elements in said catalyst and (2) at least one heat-decomposable salt formed as a by-product when at least one of said molybdates and/or tungstates is formed is dried to form a precatalyst precipitate and said precipitate is then calcined to produce said catalyst, the improvement wherein the key catalytic phase of said catalyst comprising a molybdate and/or tungsten of Bi, Te, Sb, Sn, Cu or mixtures thereof is preformed prior to combining with the other elements of said catalyst, and said aqueous slurry is dried without filtration so that said precipitate contains at least one of said heat-decomposable salts, said catalyst having a composition defined by the formula:

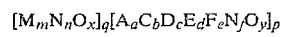

wherein
M=Bi, Te, Sb, Sn and/or Cu
N=Mo and/or W
A=alkali, Tl, and/or Sm
C=Ni, Co, Mn, Mg, Be, Ca, Sr, Ba, Zn, Cd and/or Hg
D=Fe, Cr, Ce and/or V
E=P, As, B, Sb
F=rare earth, Ti, Zr, Nb, Ta, Re, Ru, Rh, Ag, Au, Al, Ga, In, Si, Ge, Pb, Th, and/or U, and further wherein
a=0-4
b=0-20
c=0.01-20
d=0-4
e=0-8
f=8-16
m=0.01-10
n=0.1-30
a+b+c+d+e>0, and
x and y are numbers such that the valence requirements of the other elements for oxygen in the key catalytic phase and the host-catalytic phase, respectively, are satisfied; and the ratio q/p is 0.1 to 10.

4. The process of claim 3 wherein said key catalytic phase is a bismuth molybdate.

5. The process of claim 4 wherein said key catalytic phase is made by coprecipitation to form an aqueous slurry.

6. The process of claim 5 wherein the Bi/Mo ratio in said slurry is 9:1 to 1:9.

7. The process of claim 6 wherein said Bi/Mo ratio is 2:1 to 1:3.

8. The process of claim 7 wherein said Bi/Mo ratio is 2:1 to 2:3.

9. The process of claim 6 wherein the elements constituting said catalyst other than the elements in said key catalytic phase constitute a host-catalyst phase, said host-catalyst phase being preformed in an aqueous slurry prior to admixing with said precatalyst phase.

10. The process of claim 9 wherein said preformed host-catalyst phase is added to the key catalytic phase slurry without filtering said key catalytic phase slurry.

11. The process of claim 6 wherein the elements constituting said catalyst other than elements in said key catalytic phase constitute a host-catalyst phase, the compounds capable of yielding the elements of said host-catalyst phase being added to the preformed key catalytic phase aqueous slurry.

* * * * *